(12) United States Patent
Keall et al.

(10) Patent No.: US 8,457,717 B2
(45) Date of Patent: Jun. 4, 2013

(54) METHOD AND SYSTEM OF ADAPTIVE CONTROL FOR REDUCING MOTION ARTIFACTS AND PATIENT DOSE IN FOUR DIMENSIONAL COMPUTED TOMOGRAPHY

(75) Inventors: Paul J. Keall, Richmond, VA (US); Jeffrey F. Williamson, Richmond, VA (US)

(73) Assignee: Stanford University, Palo Alto, CA (US)

( * ) Notice: Subject to any disclaimer, the term of this patent is extended or adjusted under 35 U.S.C. 154(b) by 991 days.

(21) Appl. No.: 10/599,084

(22) PCT Filed: Apr. 7, 2005

(86) PCT No.: PCT/US2005/011544
§ 371 (c)(1),
(2), (4) Date: Jun. 15, 2007

(87) PCT Pub. No.: WO2005/099382
PCT Pub. Date: Oct. 27, 2005

(65) Prior Publication Data
US 2007/0286331 A1 Dec. 13, 2007

Related U.S. Application Data

(60) Provisional application No. 60/560,251, filed on Apr. 8, 2004.

(51) Int. Cl.
*A61B 5/055* (2006.01)
*H04B 15/00* (2006.01)
*G21K 5/00* (2006.01)

(52) U.S. Cl.
USPC .............................. 600/425; 702/189; 378/64

(58) Field of Classification Search
None
See application file for complete search history.

(56) References Cited

U.S. PATENT DOCUMENTS

| | | | |
|---|---|---|---|
| 5,271,055 A * | 12/1993 | Hsieh et al. | 378/95 |
| 6,076,005 A * | 6/2000 | Sontag et al. | 600/413 |
| 6,298,260 B1 * | 10/2001 | Sontag et al. | 600/413 |
| 6,690,965 B1 * | 2/2004 | Riaziat et al. | 600/428 |
| 6,959,266 B1 * | 10/2005 | Mostafavi | 702/189 |
| 7,182,083 B2 * | 2/2007 | Yanof et al. | 128/204.23 |
| 7,191,100 B2 * | 3/2007 | Mostafavi | 702/189 |
| 7,393,329 B1 * | 7/2008 | Wong et al. | 600/534 |
| 7,720,518 B2 * | 5/2010 | Motomura et al. | 600/407 |
| 7,769,430 B2 * | 8/2010 | Mostafavi | 600/428 |
| 2004/0034300 A1 | 2/2004 | Verard et al. | |
| 2004/0081270 A1 | 4/2004 | Heuscher | |
| 2004/0082853 A1 * | 4/2004 | Sasaki et al. | 600/428 |
| 2005/0113673 A1 * | 5/2005 | Avinash et al. | 600/413 |

OTHER PUBLICATIONS

George et al. "Audio-Visual Biofeedback for Respiratory-Gated Radiotherapy: Impact of Audio Instruction and Audio-Visual Biofeedback of Respiratory-Gated Radiotherapy." Int J Radiation Oncology Biol Phys, vol. 65, No. 3, pp. 924-933, 2006.*

* cited by examiner

*Primary Examiner* — Long V. Le
*Assistant Examiner* — Angela M Hoffa
(74) *Attorney, Agent, or Firm* — Whitham, Curtis, Christofferson & Cook, P.C.

(57) ABSTRACT

Motion artifacts and patient dose during 4D CT imaging are reduced by adaptive control of data acquisition. The respiration signal (310) and CT data acquisition (340) are linked, such that 'bad' data from erratic breathing cycles that cause artifacts is not acquired by pausing CT data acquisition (360) when erratic breathing is detected, and not resuming CT data acquisition until steady-state respiration is resumed. Training data is used to develop a tolerance envelope for a respiratory signal such that for erratic breathing cycles the respiratory signal is not within the tolerance envelope (330).

12 Claims, 7 Drawing Sheets

METHOD AND SYSTEM OF ADAPTIVE CONTROL FOR REDUCING MOTION ARTIFACTS AND PATIENT DOSE IN FOUR DIMENSIONAL COMPUTED TOMOGRAPHY

This application claims the benefit of U.S. Provisional Application No. 60/560,251 titled "AN ADAPTIVE CONTROL METHOD FOR ACQUIRING 4D THORACIC CT SCANS" filed on Apr. 8, 2004.

BACKGROUND OF THE INVENTION

1. Field of the Invention

The present invention generally relates to thoracic radiology, and more particularly to techniques for thoracic radiology that account for respiratory motion during four-dimensional computed tomography (4D CT).

2. Background Description

Respiratory motion creates several problems for thoracic radiology. It degrades anatomic position reproducibility during imaging. It necessitates larger margins during radiotherapy planning. And it causes errors during radiation delivery. Clinically significant lung tumor motion cannot be predicted by any known clinical parameters, suggesting that tumor motion must be explicitly determined for each patient. In fact, recent European Organization for Research and Treatment of Cancer (EORTC) guidelines state that "An assessment of 3D tumor mobility is essential for treatment planning and delivery in lung cancer."

Existing methods to account for respiratory motion during CT imaging include breath-hold, respiratory gating, and 4D CT. Four-dimensional thoracic CT images that account for respiratory motion have successfully been acquired using single-slice scanners, however, the authors of these works acknowledge the temporal and spatial limitations of 4D acquisition with current single-slice technology. Multi-slice 4D CT scans have been acquired using an axial/cine method at Washington University, Memorial Sloan Kettering Cancer Center, and Massachusetts General Hospital and by using a helical method at the MD Anderson Cancer Center. Four-dimensional cone-beam CT scans have been acquired using a benchtop system by Taguchi as well as clinically at the Netherlands Cancer Institute. Four-dimensional CT scans can be used to determine tumor motion and tumor-motion-encompassing treatment volumes—in the absence of respiratory management devices—as well as to employ the data for 4D planning and delivery. Individual phases of the 4D CT scan can be used for respiratory gated radiotherapy planning.

The use of 4D thoracic CT has been developed for and applied to radiation oncology patients. However, high-quality 4D CT data, along with accurate deformable image-registration algorithms to automate analysis of this data, could play an important role in the analysis of lung function for a variety of pulmonary diseases. The changes in local density of the lung as a function of respiration could be automatically detected and the abnormal regions displayed, leading to faster diagnosis.

Current 4D thoracic CT techniques build on those existing for cardiac imaging, in which the cardiac signal is input to the CT scanner during the sinogram evolution, from which image reconstruction at several cardiac phases can occur. However, although successive cardiac cycles are relatively reproducible under non-stressed conditions, a factor limiting the success of 4D thoracic CT is the irregularity of respiratory cycles in both displacement and cycle-to-cycle periods. Irregularity manifests itself as imaging artifacts, leading to anatomical mismatches, or there is insufficient acquisition of projection data to reconstruct a full image.

Figure 1:
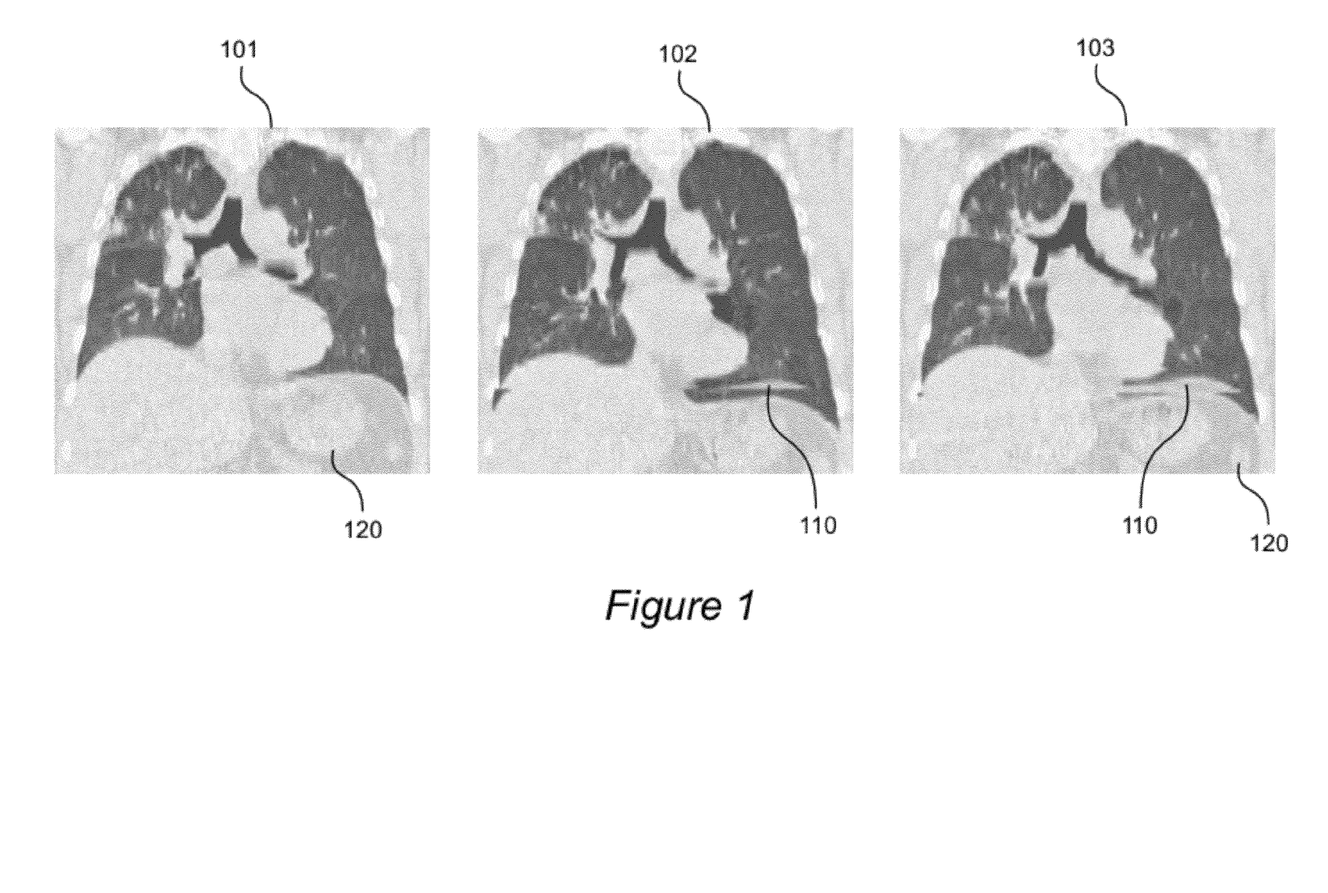
FIG. 1 shows coronal images from a 4D CT at three respiratory phases for a patient undergoing audiovisual breathing training.

To reduce this irregularity, audio and audiovisual breathing-training methods have been applied to try to improve the quality of 4D thoracic CT data. However, even with audiovisual breathing training, respiration irregularities remain as shown in FIG. 1. FIG. 1 shows coronal images from a 4D CT scan at three respiratory phases for a patient undergoing breathing training. While the left image 101 in FIG. 1 is artifact free, there is an artifact 110 near the dome of the right diaphragm 120 in the center 102 and right 103 images. Thus, whilst taking a similar approach to 4D cardiac CT methods is a good first approximation, further development is necessary to improve 4D CT acquisition.

Four-dimensional computed tomography (4D CT) acquisition methods that explicitly account for respiratory motion have been developed recently in academic and commercial settings. 4D CT is generally acquired either by sinogram or image sorting based on a post-acquisition procedure using external respiration signals. The patient's ability to maintain reproducible respiratory signals is the limiting factor during 4D CT. Methods of breathing coaching, e.g., audiovisual biofeedback, can improve respiration reproducibility, however, significant variations remain and cause artifacts in the 4D CT scan.

SUMMARY OF THE INVENTION

It is therefore an object of the present invention to provide a system and method to reduce these artifacts and their subsequent effects during radiotherapy planning and delivery.

A further object of the invention is to provide a system and method for improved 4D CT image acquisition that relies on adaptive control during data acquisition.

The invention is a method and system for reducing motion artifacts and patient dose in radiological imaging using four dimensional computed tomography (4D CT). The method identifies artifacts in 4D CT images of an anatomy being imaged, where the image artifacts are the product of irregularities in a periodic motion of the anatomy being imaged. Then the periodic motion of the anatomy is measured so as to detect the irregularities, and then a 4D CT scan of the anatomy is controlled so as to pause the scan when these irregularities are detected.

While the invention can be applied to thoracic and abdominal organs having periodic motion, those skilled in the art will be able to understand and practice the invention from its application to the lung, as described in detail below. In summary, the respiration signal and CT data acquisition are linked, such that 'bad' data from erratic breathing cycles, which cause artifacts, is not acquired. This is done by pausing CT acquisition until steady state respiration is resumed. A proof-of-principle application of the adaptive control method to an existing respiration signal, acquired during 4D CT, demonstrates the capacity of this method to reduce artifacts currently found in 4D CT scans.

An approach complimentary to breathing training to improve respiration reproducibility is to recognize irregularities and modify the scan acquisition itself. Rather than acquiring the respiration signal and CT data independently to create the 4D CT through postprocessing, the scan acquisition could be modified such that projection data from irregular breathing cycles would be ignored or not acquired at all, and sufficient projection data from regular respiration cycles would be acquired to obtain a 4D thoracic CT with minimum artifacts.

Thus, the invention demonstrates an adaptive control algorithm that takes as input the respiration signal and, based on this input, controls the CT scanner during the acquisition of a 4D thoracic CT scan to reduce the magnitude of artifacts introduced by irregular respiration.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

The adaptive control method described below requires a respiratory monitoring system to be tightly integrated into the CT scan control and interactive control of both the CT acquisition and the couch motion. The method is comprised of several pre-scan steps, the CT data acquisition itself, and post-acquisition processing.

Figure 2:
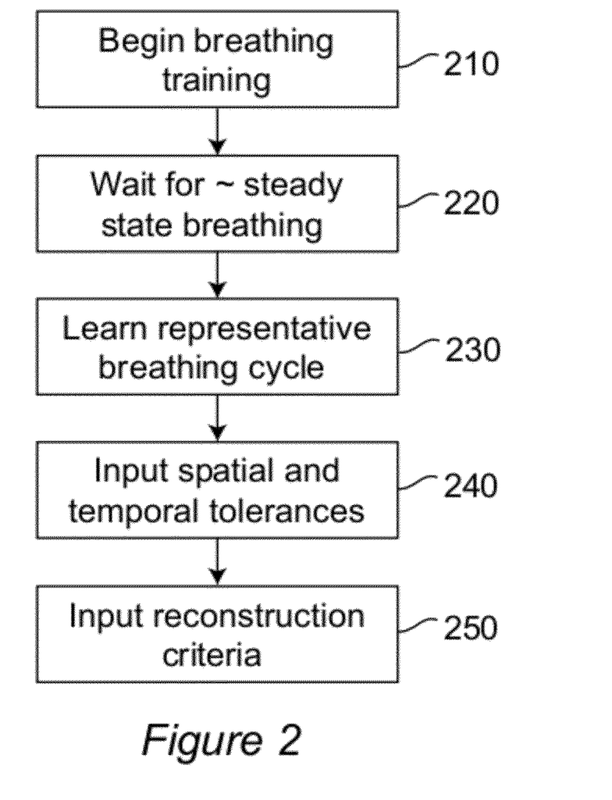
FIG. 2 is a diagram showing pre-scan procedures for an adaptive 4D CT process.

The first step, as described in Box 1 (item 210) of FIG. 2, involves breathing training. Based on data collected on lung cancer patients at Virginia Commonwealth University, the use of audiovisual breathing training significantly improves respiratory reproducibility. Box 2 (item 220) of FIG. 2 covers how a patient must be given time to fall into a reasonably regular breathing pattern. Once breathing is regular, the next step, as shown in Box 3 (item 230) of FIG. 2, is to learn the respiration pattern of an average breathing cycle. Spatial and temporal tolerances for which data acquisition will/will not occur are given in Box 4 (item 240) of FIG. 2. The tolerance set will balance acquisition time vs. image quality. The larger the tolerances, the faster the acquisition as more of the breathing cycle will be within specifications. However, more motion during image acquisition will also occur and manifest itself as image artifacts. Due to the variation within breathing cycles, a preset lower limit for the tolerances can be calculated based on the respiration patterns of the data used to learn the average breathing cycle. In Box 5 (item 250) of FIG. 2, the reconstruction criteria are input. This could be a single scan acquired at a given point in the breathing cycle, e.g., end inhale, or multiple scans acquired at several points throughout the respiratory cycle.

Once the pre-scan procedures are completed, the scan itself can occur. A flowchart of the adaptive control method for 4D CT is given in FIG. 3. In summary, the normal 4D CT scan of the patient is adaptively controlled by an analysis of the patient's respiration signal, so that the scan is paused when the respiration signal is out of tolerance. The respiration signal is acquired 310, and a determination is made 330 whether the respiration signal is within tolerance, using the tolerances set in Box 4 (item 240) of FIG. 2. If the respiration signal is within tolerance, a determination is made 320 whether sufficient data has been acquired for reconstruction, which depends upon the input reconstruction criteria input in Box 5 (item 250) of FIG. 2. If sufficient data for reconstruction has not yet been acquired, CT data acquisition continues 340. If sufficient data has been acquired for reconstruction, then the couch on which the patient lies is moved and the foregoing process is repeated until the normal process of the 4D CT scan is complete.

Figure 3:
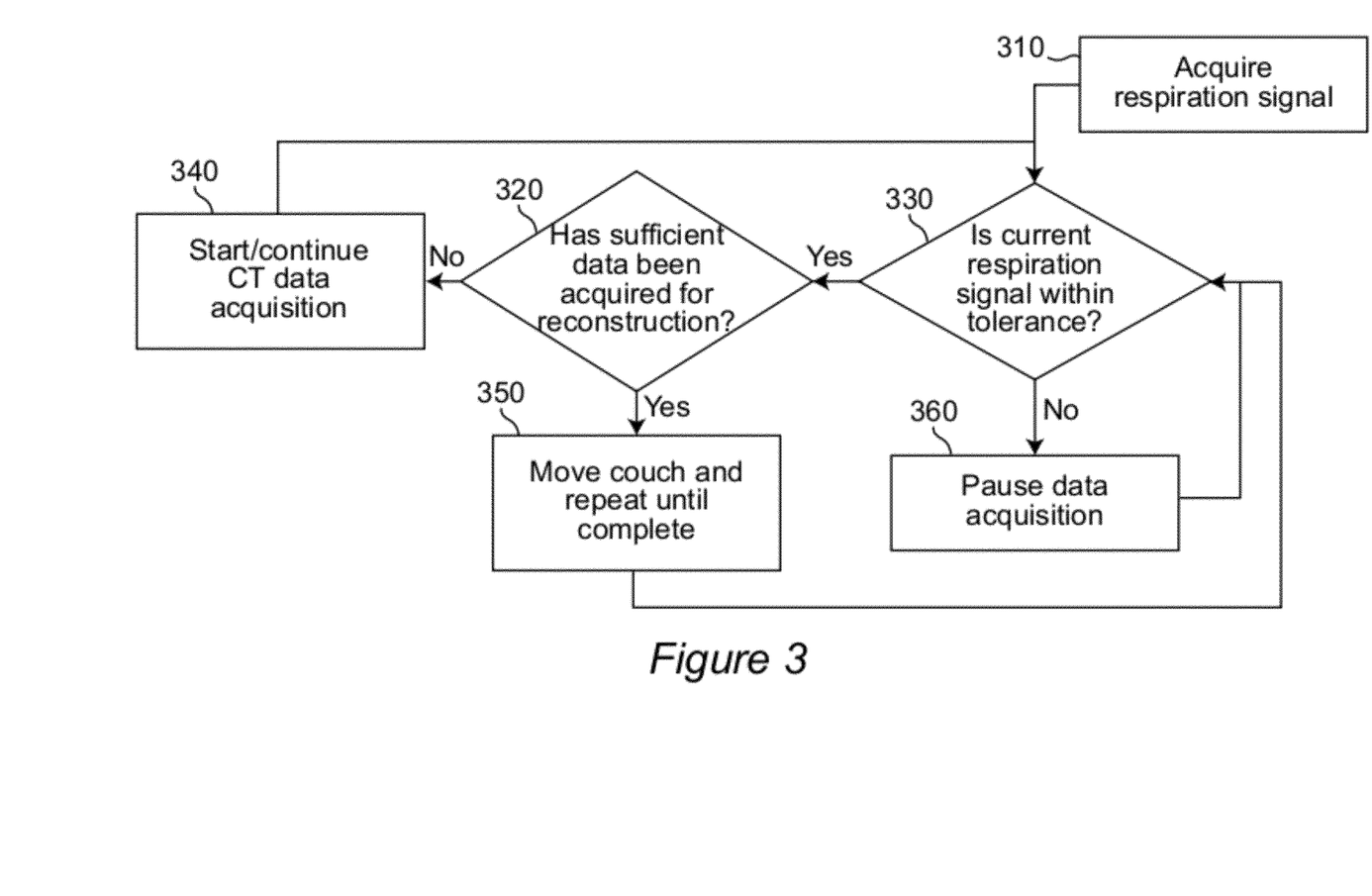
FIG. 3 is a flow chart showing adaptive CT control during CT data acquisition.

Whenever the respiration signal 310 is not within tolerance (as determined by an evaluation 330 of the respiration signal) then CT data acquisition 340 is paused 360. A tally is required to ensure that the entire geometry scanned has had sufficient data acquisition to ensure that reconstruction without missing data can occur. After acquisition, image reconstruction can automatically occur based on the requirements input in Box 5 (item 250) of FIG. 2.

Figure 4A:
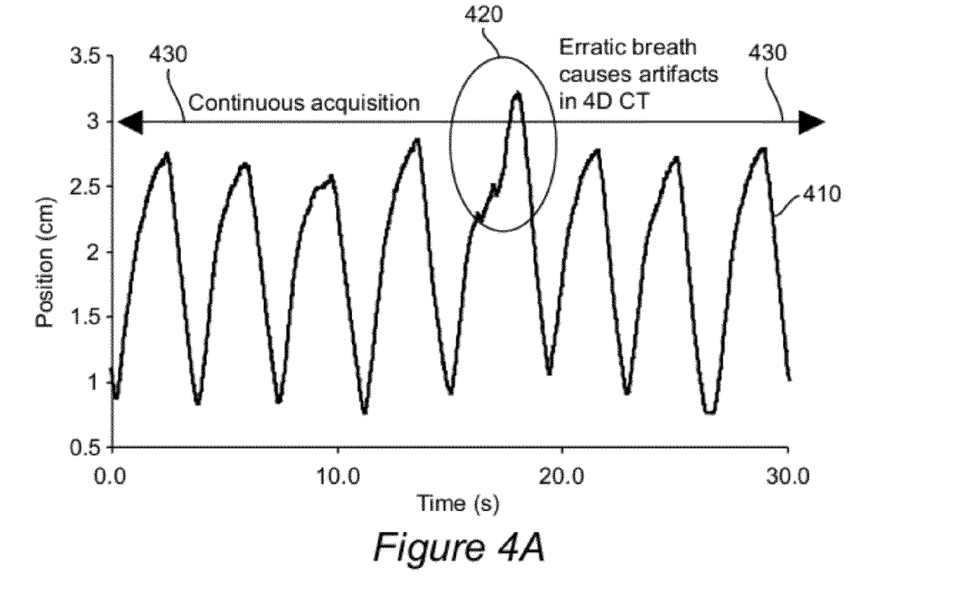
FIG. 4a is a graph of a respiration signal showing an erratic respiration cycle causing artifacts in the corresponding 4D CT image.

The method of the invention will now be demonstrated with reference to FIG. 4. The conventional 4D CT scan is represented by the graph in FIG. 4a. The 4D CT scan itself over time is represented by the line 430. The patient's respiration is shown by signal 410. An erratic breath 420 causes artifacts in the 4D CT scan (as shown earlier in FIG. 1). In the conventional 4D CT scan there is no adaptive control of the scan based on the respiration signal.

Figure 4B:
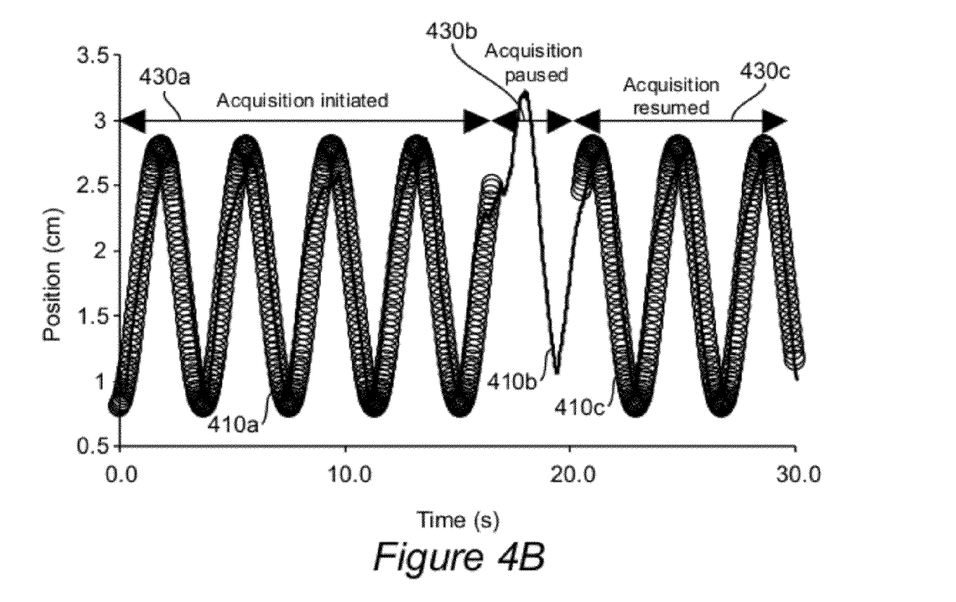
FIG. 4b is a graph of the same signal as in FIG. 4a, within an envelope of spatial and temporal tolerances, showing pausing of data acquisition during the erratic respiration cycle.

Now turning to FIG. 4b, there is shown a tolerance envelope around respiration signal 410, in particular in signal segments 410a and 410c. It will be observed that the respiration signal is not within the tolerance envelope in the respiration cycle 410b, where the respiration signal is shown without a tolerance envelope. In accordance with the invention, as more particularly described with reference to FIG. 3, the 4D CT data acquisition is initiated and proceeds during time period 430a, is paused during time period 430b corresponding to the time period during which the respiration cycle 410b is not within the tolerance envelope, and then resumes during time period 430c.

Figure 5A:
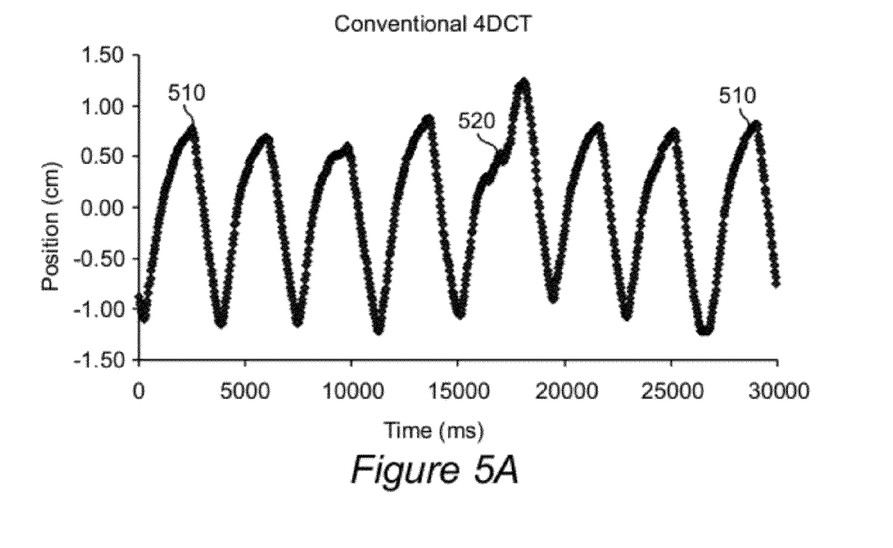
FIG. 5a is a graph of a conventional 4D CT respiration signal.
Figure 5B:
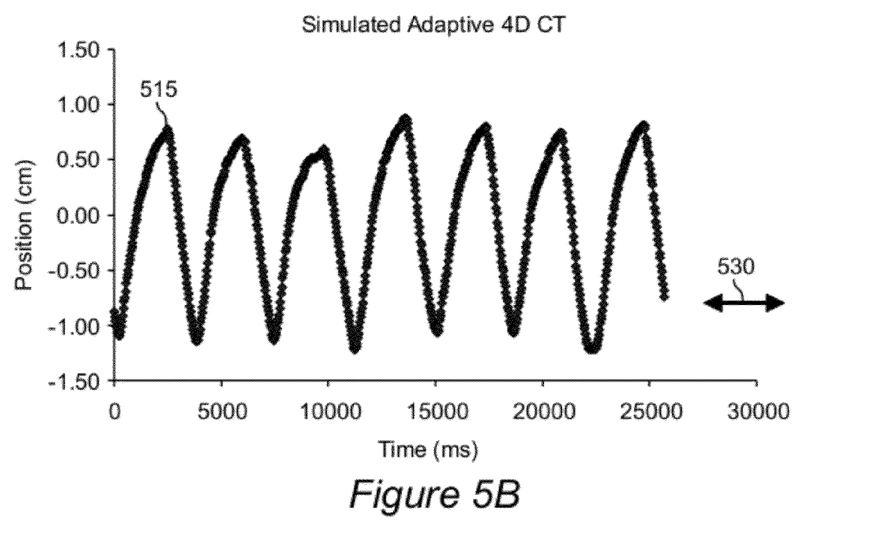
FIG. 5b is a simulated respiration signal using adaptive 4D CT.

A simulation of the results of operation of the invention as described above with reference to FIG. 4 will now be shown with reference to FIG. 5. In order to simulate the adaptive 4D CT, we took the unaltered respiration trace of a patient undergoing 4D CT acquisition and also removed the irregular breathing trace to simulate an adaptive 4D CT acquisition. These traces are shown in FIG. 5. The respiration signal 510 in FIG. 5a is very regular apart from a single erratic respiration cycle 520 (corresponding to the erratic breath 420 shown in FIG. 4a) that, under continuous acquisition (i.e. represented by line 430 in FIG. 4a), causes artifacts in the 4D CT image. An adaptive CT acquisition pauses the acquisition once the irregular respiration signal is detected and then restarts data acquisition once steady-state breathing is resumed, as described above with respect to FIG. 4b. The simulated adaptive 4D CT scan is shown in FIG. 5b, where the simulation of the scan is represented by a reconstructed respiration signal. It will be observed that the reconstructed respiration signal 515 omits the erratic respiration cycle 520, and therefore is shorter than respiration signal 510 by the amount 530, which is the time represented by the omitted respiration cycle 520. It will also be observed that the adaptive control linkage between the respiration signal and CT data acquisition means that, in the preferred embodiment of the invention, this omission also reduces the dose the patient receives during the 4D CT scan. While post-processing could also be used to implement the invention by removing data acquired during erratic respiration cycle 520, this is not the preferred embodiment.

Figure 6A:
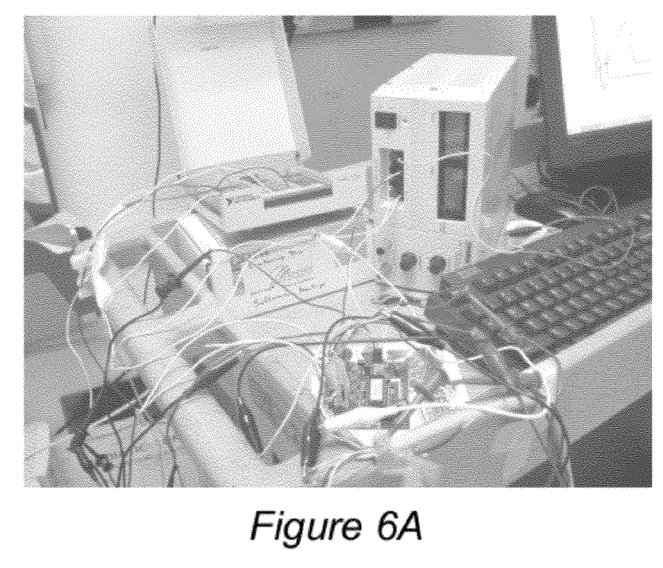
FIG. 6a is a picture of hardware used to control the stepper motion of a motion platform for a simulated 4D CT scan.
Figure 6B:
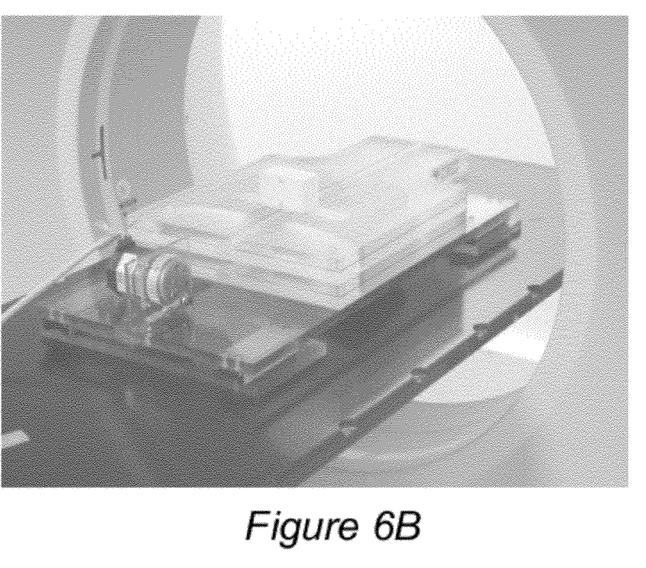
FIG. 6b is a picture of an anthropomorphic phantom with lung inserts riding on the motion platform.
Figure 7A:
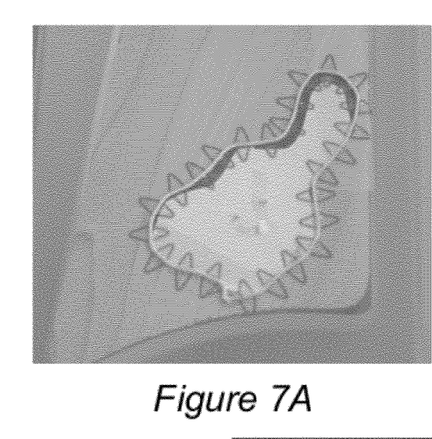
FIG. 7a shows the anatomy imaged.
Figure 7B:
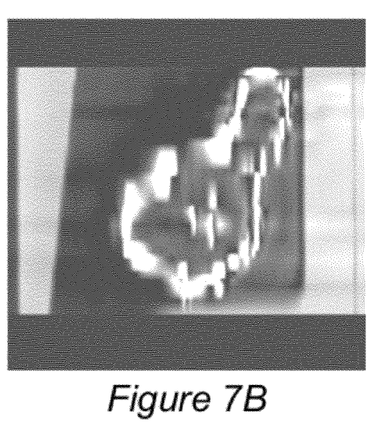
FIGS. 7b and 7c show adaptive coronal 4D CT images at inhale and exhale, respectively.
Figure 7C:
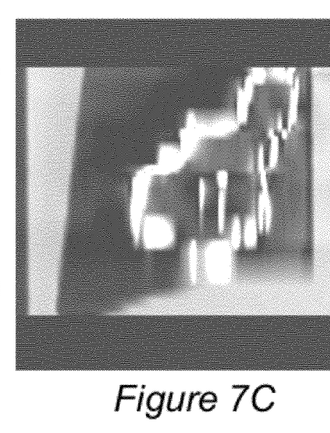
Figure 7D:
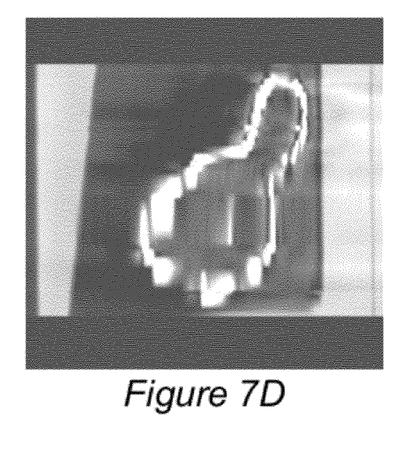
FIGS. 7d and 7e show conventional coronal 4D CT images at inhale and exhale, respectively.
Figure 7E:
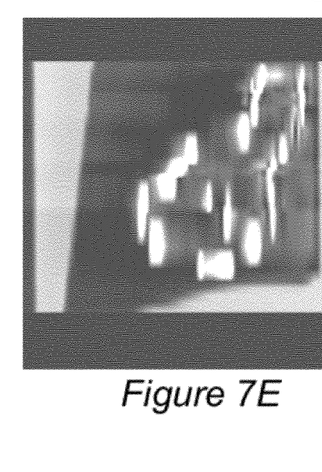

In the simulation a motion control system was programmed to read in a respiration trace (the trace shown in FIG. 5a) and control a stepper motor movement. A photograph of the control system is shown in FIG. 6a. The respiration traces were repeated until the completion of the 4D CT scan. The stepper motor drove a mechanical motion platform. An anthropomorphic phantom with lung inserts was placed on the motion platform, as shown in FIG. 6b.

Coronal images for the inhale and exhale phases of a 4D CT scan can be compared for conventional and adaptive approaches as will now be shown with reference to FIG. 7. The anatomy to be imaged is shown in FIG. 7a. The inhale phase for the adaptive 4D CT scan is shown in FIG. 7b, as compared to the inhale phase for the conventional 4D CT scan shown in FIG. 7c. Similarly, the exhale phase for the adaptive 4D CT scan is shown in FIG. 7d, as compared to the exhale phase for the conventional 4D CT scan shown in FIG. 7e. It is evident that the simulated adaptive controlled images show reduced motion artifacts as compared with the conventional 4D CT images, particularly for the exhale phase.

The method described above is flexible enough to allow both sequential axial and helical 4D CT acquisition, however, the axial approach is the preferred implementation. The adaptive 4D CT method can minimize dose to the patient in two ways: (1) by pausing acquisition during irregular breathing and (2) by stopping acquisition once sufficient information has been acquired to reconstruct the 4D CT scan.

The use of 4D thoracic CT has been developed for and applied to radiation oncology patients. However, high-quality 4D CT data, along with accurate deformable image-registration algorithms to automate analysis of this data, could play an important role in the analysis of lung function for a variety of pulmonary diseases. The changes in local density of the lung as a function of respiration could be automatically detected and the abnormal regions displayed, leading to faster diagnosis. Improved 4D CT may also help improve PET/CT, which suffers from motion artifacts.

It should be acknowledged that a single respiration signal does not necessarily correlate well with other sources of respiration motion for the same patient, as demonstrated from recent data. Thus, the choice of the respiratory signal that is most highly correlated with the motion of the object of most interest is prudent.

Although the efforts here have been directed towards respiratory motion, other motion such as skeletal and gastrointestinal motion could also potentially be used for adaptive control, provided the appropriate monitoring system is integrated with the CT control system.

Four-dimensional CT methods accounting for respiratory motion are being developed primarily for radiation oncology applications. However, there is potentially a significant widespread role for 4D CT in diagnostic radiology for pulmonary function tests. Limiting the widespread application of 4D CT is the utility of current passive acquisition techniques that account for the variations in patients' respiratory signals. Active 4D CT acquisition processes, such as the adaptive control method, may potentially allow the general use of 4D CT for radiation oncology applications, as well as general diagnostic use in assessing ventilatory function.

While the invention has been described in terms of a single preferred embodiment, those skilled in the art will recognize that the invention can be practiced with modification within the spirit and scope of the appended claims.

The invention claimed is:

1. A method for reducing motion artifacts and patient dose in radiological imaging using four dimensional computed tomography (4D CT), comprising the steps of:
    identifying a pattern in an average cycle of an anatomy being imaged, said pattern being responsive to a reproducible periodic motion of said anatomy learned through training of the patient;
    establishing spatial and temporal tolerances around said pattern, said tolerances being based on data of said periodic motion learned through training of the patient and forming an envelope around said pattern balancing an acquisition time against a quality of an acquired 4D CT image;
    measuring a periodic motion of said anatomy so as to detect when said periodic motion is outside said tolerances;
    controlling a 4D CT scan of said anatomy so as to pause the scan during periods having said detected out of tolerance condition.

2. A method as in claim 1, wherein said anatomy is a lung and said measuring step uses a respiratory signal.

3. The method of claim 2, wherein said controlling step further includes the steps of:
    acquiring a respiratory signal during said 4D CT scan;
    applying said envelope to said respiratory signal; and
    adapting said 4D CT scan to said respiratory signal by excluding from said 4D CT scan data acquired when said respiratory signal is not within said envelope.

4. The method of claim 3, wherein data acquired during irregular respiratory cycles is excluded by pausing said 4D CT scan data acquisition when said respiratory signal is not within said envelope.

5. A system for reducing motion artifacts and patient dose in radiological imaging using four dimensional computed tomography (4D CT), comprising a non-transitory computer-readable medium with instructions that when executed by a processor perform the following steps:
    identifying a pattern in an average cycle of an anatomy being imaged, said pattern being responsive to a reproducible periodic motion of said anatomy learned through training of the patient;
    establishing spatial and temporal tolerances around said pattern, said tolerances being based on data of said periodic motion learned through training of the patient and forming an envelope around said pattern balancing an acquisition time against a quality of an acquired 4D CT image;
    measuring a periodic motion of said anatomy so as to detect when said periodic motion is outside said tolerances;
    controlling a 4D CT scan of said anatomy so as to pause the scan during periods having said detected out of tolerance condition.

6. A system as in claim 5, wherein said anatomy is a lung and said measuring step uses a respiratory signal.

7. The system of claim 6, wherein said controlling step further comprises:
    acquiring a respiratory signal during said 4D CT scan;
    applying said envelope to said respiratory signal; and adapting said 4D CT scan to said respiratory signal by excluding from said 4D CT scan data acquired when said respiratory signal is not within said envelope.

8. The system of claim 7, wherein said adapting step provides that data acquired during irregular respiratory cycles is excluded by pausing said 4D CT scan data acquisition when said respiratory signal is not within said envelope.

9. A method for reducing motion artifacts in radiological imaging using four dimensional computed tomography (4D CT), comprising the steps of:
   identifying a pattern in an average cycle of an anatomy being imaged, said pattern being responsive to a reproducible periodic motion of said anatomy learned through training of the patient;
   establishing spatial and temporal tolerances around said pattern, said tolerances being based on data of said periodic motion learned through training of the patient and forming an envelope around said pattern balancing an acquisition time against a quality of an acquired 4D CT image;
   measuring a periodic motion of said anatomy so as to detect when said periodic motion is outside said tolerances;
   controlling post-processing of a 4D CT scan of said anatomy so as to remove scan data acquired during periods having said detected out of tolerance condition.

10. A method as in claim 9, wherein said anatomy is a lung and said measuring step uses a respiratory signal.

11. The method of claim 10, wherein said controlling step further includes the steps of:
   acquiring a respiratory signal during said 4D CT scan;
   applying said envelope to said respiratory signal; and
   adapting said 4D CT scan to said respiratory signal by excluding during said post-processing of said 4D CT scan data acquired when said respiratory signal is not within said envelope.

12. The method of claim 11, wherein data acquired during irregular respiratory cycles is excluded by removing scan data acquired during said 4D CT scan when said respiratory signal was not within said envelope.

* * * * *